United States Patent
Gleicher et al.

(10) Patent No.: US 10,884,003 B2
(45) Date of Patent: Jan. 5, 2021

(54) DIAGNOSIS AND ANTI-MULLERIAN HORMONE (AMH) ADMINISTRATION FOR TREATMENT OF INFERTILITY FOR GOOD-, INTERMEDIATE- AND POOR-PROGNOSIS PATIENTS FOR IN VITRO FERTILIZATION IN VIEW OF LOGISTIC REGRESSION MODELS

(71) Applicants: American Infertility of New York, P.C., New York, NY (US); Norbert Gleicher, New York, NY (US); Vitaly Kushnir, New York, NY (US); David H. Barad, New York, NY (US)

(72) Inventors: Norbert Gleicher, New York, NY (US); Vitaly A. Kushnir, New York, NY (US); David H. Barad, Closter, NJ (US)

(73) Assignees: American Infertility of New York, P.C., New York, NY (US); Norbert Gleicher, New York, NY (US); Vitaly A. Kushnir, New York, NY (US); David H. Barad, Closter, NJ (US)

( * ) Notice: Subject to any disclaimer, the term of this patent is extended or adjusted under 35 U.S.C. 154(b) by 20 days.

(21) Appl. No.: 16/241,985

(22) Filed: Jan. 7, 2019

(65) Prior Publication Data
US 2019/0195895 A1 Jun. 27, 2019

Related U.S. Application Data

(63) Continuation of application No. 15/015,543, filed on Feb. 4, 2016, now Pat. No. 10,175,252.

(51) Int. Cl.
| | |
|---|---|
| *G01N 33/74* | (2006.01) |
| *A61K 38/24* | (2006.01) |
| *G01N 33/68* | (2006.01) |
| *A61K 38/22* | (2006.01) |

(52) U.S. Cl.
CPC .............. *G01N 33/74* (2013.01); *A61K 38/22* (2013.01); *A61K 38/24* (2013.01); *G01N 33/6893* (2013.01); *G01N 2333/575* (2013.01); *G01N 2800/368* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 7,241,577 B2 | 7/2007 | Seifer | |
| 2010/0048525 A1* | 2/2010 | Gleicher | A61K 31/57 514/178 |

FOREIGN PATENT DOCUMENTS

| | | |
|---|---|---|
| EP | 1074265 | 7/2001 |
| WO | WO 03/016514 | 2/2003 |

OTHER PUBLICATIONS

Lee et al., Reproductive Biology and Endocrinology 2011, 9: 115 (Year: 2011).*
Gada et al., Fertility and Sterility, 2011 vol. 95, No. 4, Supp. Suppl. 1, pp. S23. Abstract No. P-41 (Year: 2011).*
Josso et al., Human Reproduction Update, 2005, vol. 11, No. 4 pp. 351-356 (Year: 2005).*
Kaya et al., Fertil Steril 2010; 94:2202-7 (Year: 2010).*
Tal et al., Am J Obstet Gynecol 2014;211:59.e1-8 (Year: 2014).*
Xi et al. , J Assist Reprod Genet (2012) 29:397-402 (Year: 2012).*
Vitaly A. Kushnir, David R. Seifer, David H. Barad, Aritro Sen, Norbert Gleicher, "Potential therapeutic applications of human anti-Müllerian hormone (AMH) analogues in reproductive medicine", accepted for publication Jun. 7, 2017, Springer Science+Business Media LLC, Journal of Assisted Reproduction and Genetics.
Lidija K. Gorsic, Gulum Kosova, Brian Werstein, Ryan Sisk, Richard S. Legro, M. Geoffrey Hayes, Jose M. Teixeira, Andrea Dunaif, Margrit Urbanek, Pathogenic Anti-Müllerian Hormone Variants in Polycystic Ovary Syndrome, Aug. 2017, Journal of Clinical Endocrinology Metabolism, vol. 102(8) pp. 2862-2872.
Grynberg et al. (Human Reproduction, (Jun. 2013) vol. 28, Supp. Suppl. 1, pp. i111. Abstract No. )-269, Meeting info. 29th Annual Meeting of the European Society of Human Reproduction and Embryology ESHRE 2013, London, United Kingdom. (Year: 2013).
Bhattecharya et al. (PLoS One 2(3): e0171355. https://doi.org/10.1371/journal.pone.0171355; 22 pages total (Year: 2017).

* cited by examiner

*Primary Examiner* — Christina M Borgeest
(74) *Attorney, Agent, or Firm* — Robert J. Hess; Hess Patent Law Firm (57) ABSTRACT

Method of diagnosis of IVF viability. The method includes ascertaining a subject's AMH level from testing and then selecting one pregnancy or live birth prognosis category that applies to the ascertained AMH level by matching the ascertained AMH level with an applicable one of a plurality of ranges of AMH levels pertaining to an age of the subject. The matching indicates the prognosis category that applies, i.e., (that is, good, intermediate or poor. In view of the diagnosis, a method of administration of AMH may be pursued to increase probability of pregnancy or live birth chances. Alternatively, the administration of AMH may be at AMH levels that will terminate pregnancy or increase the chance of miscarriage.

17 Claims, 3 Drawing Sheets
Specification includes a Sequence Listing.

FIG. 1A

| | Clinical pregnancy rates | | | | |
|---|---|---|---|---|---|
| | Ages | | | | |
| Embryos | <36 | 36-38 | 39-40 | 41-42 | ≥43 |
| 1 | 34% | 24% | 20% | 15% | 6% |
| 2 | 36% | 25% | 22% | 16% | 7% |
| 3 | 38% | 27% | 23% | 17% | 7% |
| 4 | 40% | 29% | 24% | 18% | 8% |
| 5 | 42% | 30% | 26% | 19% | 8% |
| 6 | 44% | 32% | 27% | 21% | 9% |
| 7 | 46% | 34% | 29% | 22% | 10% |
| 8 | 48% | 36% | 31% | 23% | 11% |
| 9 | 50% | 37% | 33% | 25% | 11% |
| 10 | | 39% | 34% | 27% | 12% |
| 11 | | | 36% | 28% | 13% |
| 12 | | | 38% | 30% | 14% |
| 13 | | | | 31% | 15% |
| 14 | | | | | 16% |
| 15 | | | | | 17% |

| | Live birth rates | | | | |
|---|---|---|---|---|---|
| | Ages | | | | |
| Embryos | <36 | 36-38 | 39-40 | 41-42 | ≥43 |
| 1 | 29% | 17% | 15% | 8% | 3% |
| 2 | 31% | 18% | 16% | 9% | 3% |
| 3 | 32% | 19% | 17% | 10% | 3% |
| 4 | 34% | 20% | 18% | 10% | 4% |
| 5 | 36% | 21% | 19% | 11% | 4% |
| 6 | 37% | 22% | 20% | 12% | 4% |
| 7 | 39% | 23% | 21% | 12% | 4% |
| 8 | 41% | 25% | 23% | 13% | 5% |
| 9 | 42% | 26% | 24% | 14% | 5% |
| 10 | 44% | 27% | 25% | 15% | 5% |
| 11 | | 29% | 27% | 16% | 6% |
| 12 | | 30% | 28% | 17% | 6% |
| 13 | | | 30% | 18% | 7% |
| 14 | | | 31% | 19% | 7% |
| 15 | | | | 20% | 8% |

| | Clinical pregnancy rates | | | | |
|---|---|---|---|---|---|
| | Ages | | | | |
| FSH | <36 | 36-38 | 39-40 | 41-42 | ≥43 |
| 2.5 | | | | 19% | 9% |
| 5.0 | | | 24% | 17% | 8% |
| 7.5 | | 25% | 21% | 15% | 7% |
| 10.0 | 33% | 23% | 19% | 13% | 6% |
| 12.5 | 30% | 21% | 17% | 12% | 5% |
| 15.0 | 27% | 18% | 15% | 10% | 5% |
| 17.5 | 24% | 16% | 13% | 9% | 4% |
| 20.0 | 22% | 14% | 12% | 8% | 4% |
| 22.5 | 20% | 13% | 10% | 7% | 3% |
| 25.0 | 18% | 11% | 9% | 6% | 3% |
| 27.5 | 16% | 10% | 8% | 5% | 2% |
| 30.0 | 14% | 9% | 7% | 5% | 2% |
| 32.5 | 12% | 8% | 6% | 4% | 2% |
| 35.0 | 11% | 7% | 5% | 4% | 2% |
| 37.5 | 10% | 6% | 5% | 3% | 1% |
| 40.0 | 8% | 5% | 4% | 3% | 1% |

| | Live birth rates | | | | |
|---|---|---|---|---|---|
| | Ages | | | | |
| FSH | <36 | 36-38 | 39-40 | 41-42 | ≥43 |
| 2.5 | | 21% | 19% | 11% | 4% |
| 5.0 | | 19% | 17% | 10% | 3% |
| 7.5 | | 17% | 16% | 8% | 3% |
| 10.0 | 28% | 15% | 14% | 8% | 3% |
| 12.5 | 25% | 14% | 12% | 7% | 2% |
| 15.0 | 23% | 12% | 11% | 6% | 2% |
| 17.5 | 21% | 11% | 10% | 5% | 2% |
| 20.0 | 19% | 10% | 9% | 5% | 2% |
| 22.5 | 17% | 9% | 8% | 4% | 1% |
| 25.0 | 15% | 8% | 7% | 4% | 1% |
| 27.5 | 14% | 7% | 6% | 3% | 1% |
| 30.0 | 12% | 6% | 6% | 3% | 1% |
| 32.5 | 11% | 5% | 5% | 3% | 1% |
| 35.0 | 10% | 5% | 4% | 2% | 1% |
| 37.5 | 9% | 4% | 4% | 2% | 1% |
| 40.0 | 8% | 4% | 3% | 2% | 1% |

| Clinical pregnancy rates | | | | | |
|---|---|---|---|---|---|
| AMH | Ages | | | | |
| | <36 | 36-38 | 39-40 | 41-42 | ≥43 |
| 0.5 | 29% | 16% | 15% | 12% | 7% |
| 1.0 | 33% | 19% | 17% | 15% | 8% |
| 1.5 | 37% | 22% | 20% | 17% | 9% |
| 2.0 | 40% | 24% | 22% | 19% | 11% |
| 2.5 | 43% | 27% | 25% | 21% | 12% |
| 3.0 | 46% | 29% | 27% | 23% | 13% |
| 3.5 | | 31% | 29% | 25% | 15% |
| 4.0 | | 33% | 31% | 27% | 16% |
| 4.5 | | | 32% | 28% | |
| 5.0 | | | | | |
| 5.5 | | | | | |
| 6.0 | | | | | |
| 6.5 | | | | | |
| 7.0 | | | | | |
| 7.5 | | | 32% | 28% | |
| 8.0 | | 34% | 31% | 27% | 16% |
| 8.5 | | 32% | 30% | 26% | 15% |
| 9.0 | 48% | 31% | 28% | 24% | 14% |
| 9.5 | 45% | 28% | 26% | 22% | 13% |
| 10.0 | 42% | 26% | 23% | 20% | 11% |

| Live birth rates | | | | | |
|---|---|---|---|---|---|
| AMH | Ages | | | | |
| | <36 | 36-38 | 39-40 | 41-42 | ≥43 |
| 0.5 | 25% | 11% | 11% | 7% | 3% |
| 1.0 | 29% | 13% | 13% | 9% | 3% |
| 1.5 | 32% | 15% | 15% | 10% | 4% |
| 2.0 | 36% | 18% | 17% | 11% | 4% |
| 2.5 | 39% | 19% | 19% | 13% | 5% |
| 3.0 | 41% | 21% | 21% | 14% | 5% |
| 3.5 | | 23% | 22% | 15% | 6% |
| 4.0 | | | | | 6% |
| 4.5 | | | | | 6% |
| 5.0 | | | | | 7% |
| 5.5 | | | | | 6% |
| 6.0 | | | | | 6% |
| 6.5 | | | | | 6% |
| 7.0 | | 22% | 22% | 15% | 6% |
| 7.5 | 41% | 21% | 20% | 14% | 5% |
| 8.0 | 38% | 19% | 18% | 13% | 5% |
| 8.5 | 35% | 17% | 16% | 11% | 4% |
| 9.0 | 32% | 15% | 14% | 10% | 4% |
| 9.5 | 28% | 13% | 12% | 8% | 3% |
| 10.0 | 24% | 11% | 10% | 7% | 2% |

FIG. 3D

SEQUENCE LISTING

<160> NUMBER OF SEQ ID NOS: 1

<210> SEQ ID NO 1
<211> LENGTH: 560
<212> TYPE: PRT
<213> ORGANISM: Homo sapiens

<400> SEQUENCE: 1

Met Arg Asp Leu Pro Leu Thr Ser Leu Ala Leu Val Leu Ser Ala Leu
1               5                   10                  15

Gly Ala Leu Leu Gly Thr Glu Ala Leu Arg Ala Glu Glu Pro Ala Val
            20                  25                  30

Gly Thr Ser Gly Leu Ile Phe Arg Glu Asp Leu Asp Trp Pro Pro Gly
        35                  40                  45

Ser Pro Gln Glu Pro Leu Cys Leu Val Ala Leu Gly Gly Asp Ser Asn
    50                  55                  60

Gly Ser Ser Ser Pro Leu Arg Val Val Gly Ala Leu Ser Ala Tyr Glu
65                  70                  75                  80

Gln Ala Phe Leu Gly Ala Val Gln Arg Ala Arg Trp Gly Pro Arg Asp
                85                  90                  95

Leu Ala Thr Phe Gly Val Cys Asn Thr Gly Asp Arg Gln Ala Ala Leu
            100                 105                 110

Pro Ser Leu Arg Arg Leu Gly Ala Trp Leu Arg Asp Pro Gly Gly Gln
        115                 120                 125

Arg Leu Val Val Leu His Leu Glu Glu Val Thr Trp Glu Pro Thr Pro
    130                 135                 140

Ser Leu Arg Phe Gln Glu Pro Pro Gly Gly Ala Gly Pro Pro Glu
145                 150                 155                 160

Leu Ala Leu Leu Val Leu Tyr Pro Gly Pro Gly Pro Glu Val Thr Val
                165                 170                 175

Thr Arg Ala Gly Leu Pro Gly Ala Gln Ser Leu Cys Pro Ser Arg Asp
            180                 185                 190

Thr Arg Tyr Leu Val Leu Ala Val Asp Arg Pro Ala Gly Ala Trp Arg
        195                 200                 205

Gly Ser Gly Leu Ala Leu Thr Leu Gln Pro Arg Gly Glu Asp Ser Arg
    210                 215                 220

Leu Ser Thr Ala Arg Leu Gln Ala Leu Leu Phe Gly Asp Asp His Arg
225                 230                 235                 240

Cys Phe Thr Arg Met Thr Pro Ala Leu Leu Leu Pro Arg Ser Glu
                245                 250                 255

Pro Ala Pro Leu Pro Ala His Gly Gln Leu Asp Thr Val Pro Phe Pro
            260                 265                 270

Pro Pro Arg Pro Ser Ala Glu Leu Glu Glu Ser Pro Pro Ser Ala Asp
        275                 280                 285

Pro Phe Leu Glu Thr Leu Thr Arg Leu Val Arg Ala Leu Arg Val Pro
    290                 295                 300

Pro Ala Arg Ala Ser Ala Pro Arg Leu Ala Leu Asp Pro Asp Ala Leu
305                 310                 315                 320

Ala Gly Phe Pro Gln Gly Leu Val Asn Leu Ser Asp Pro Ala Ala Leu
                325                 330                 335

Glu Arg Leu Leu Asp Gly Glu Glu Pro Leu Leu Leu Leu Arg Pro
            340                 345                 350

Thr Ala Thr Thr Gly Asp Pro Ala Pro Leu His Asp Pro Thr Ser
        355                 360                 365

-continued

```
Ala Pro Trp Ala Thr Ala Leu Ala Arg Arg Val Ala Ala Glu Leu Gln
    370                 375                 380
Ala Ala Ala Ala Glu Leu Arg Ser Leu Pro Gly Leu Pro Pro Ala Thr
385                 390                 395                 400
Ala Pro Leu Leu Ala Arg Leu Leu Ala Leu Cys Pro Gly Gly Pro Gly
            405                 410                 415
Gly Leu Gly Asp Pro Leu Arg Ala Leu Leu Leu Lys Ala Leu Gln
            420                 425                 430
Gly Leu Arg Val Glu Trp Arg Gly Arg Asp Pro Arg Gly Pro Gly Arg
        435                 440                 445
Ala Gln Arg Ser Ala Gly Ala Thr Ala Ala Asp Gly Pro Cys Ala Leu
    450                 455                 460
Arg Glu Leu Ser Val Asp Leu Arg Ala Glu Arg Ser Val Leu Ile Pro
465                 470                 475                 480
Glu Thr Tyr Gln Ala Asn Asn Cys Gln Gly Val Cys Gly Trp Pro Gln
                485                 490                 495
Ser Asp Arg Asn Pro Arg Tyr Gly Asn His Val Val Leu Leu Leu Lys
            500                 505                 510
Met Gln Val Arg Gly Ala Ala Leu Ala Arg Pro Pro Cys Cys Val Pro
        515                 520                 525
Thr Ala Tyr Ala Gly Lys Leu Leu Ile Ser Leu Ser Glu Glu Arg Ile
    530                 535                 540
Ser Ala His His Val Pro Asn Met Val Ala Thr Glu Cys Gly Cys Arg
545                 550                 555                 560
```

DIAGNOSIS AND ANTI-MULLERIAN HORMONE (AMH) ADMINISTRATION FOR TREATMENT OF INFERTILITY FOR GOOD-, INTERMEDIATE- AND POOR-PROGNOSIS PATIENTS FOR IN VITRO FERTILIZATION IN VIEW OF LOGISTIC REGRESSION MODELS

REFERENCE TO COPENDING PATENT APPLICATIONS

The present utility patent application is a continuation of U.S. utility patent application Ser. No. 15/015,543, which was filed Feb. 4, 2016.

REFERENCE TO SEQUENCE LISTING SUBMITTED VIA EFS-WEB

This application includes an electronically submitted sequence listing in .txt format. The .text file contains a sequence listing entitled "CHR-1-CON_ST25.txt" created on Mar. 2, 2018 and is 5,352 bytes in size. The sequence listing contained in .txt format is part of this specification and is identical to that filed with U.S. utility patent application Ser. No. 15/015,543, whose contents are incorporated herein by reference. The .txt file filed with that patent application contains a sequence listing entitled "CHR-1_ST25.txt" created on Mar. 2, 2018 and is 5,352 bytes in size.

BACKGROUND OF THE INVENTION

Field of the Invention

The invention relates to categories of good, intermediate and poor prognosis for in vitro fertilization (IVF) according to age of a candidate for IVF. By ascertaining the anti-Mullerian hormone (AMH) level for such a candidate with conventional testing, a diagnosis, and then therapy, in accordance with the invention may be made as to the prognosis category that applies for pregnancy probability, live birth probability or both by matching the tested AMH level with an applicable one of ranges of AMH levels of the prognosis categories in correspondence with the age of the candidate.

The invention then specifically relates to the administration of AMH in view of the logistic regression models that so classify patients or subjects into the good-, intermediate- and poor-prognosis groups or categories. Patients or subjects can be classified into good-, intermediate- and poor-prognosis categories based on clinical pregnancy and live birth rates, using only age and functional ovarian reserve parameters. AMH is expressed by a specific category of follicular cells called granulosa cells of preantral and antral follicles during the reproductive age. AMH acts as a natural follicular gatekeeper limiting follicle growth initiation and maintains the primordial follicle pool throughout the reproductive age.

AMH is also known as a Mullerian inhibiting substance (MIS) and is a member of the large transforming growth factor-beta (TGF beta) family of glycoproteins that are involved in the regulation of growth and differentiation. This family includes AMH agonists, derivatives and other TGF beta agents.

Description of Related Art

The contents of U.S. provisional patent application No. 62/128,127 are incorporated herein by reference pertaining to preparation of a composition having AMH and its administration to a subject. Further, the entire subject matter under the heading "Definitions" of that application are incorporated herein by reference. Furthermore, the term AMH as used in this application includes AMH agonists, AMH derivatives and other TGF beta agents and MISs.

An AMH test may involve taking a blood sample from the subject in a conventional manner and analyzing the blood sample with appropriate conventional laboratory test procedures and equipment. Laboratory test procedures and equipment to ascertain an AMH level are conventionally known. For example, the Becknman Coulter Diagnostics Access AHM Assay may be used in an analysis to ascertain the AMH level of a subject.

For this invention, AMH was assessed with such Generation II (second generation) assays. Those skilled in the art will understand that other generations of assays and conventional test procedures could be used as well. While AMH assays may vary at the extremes of very high or very low AMH levels, they are very similar in the medium and other ranges significant for this invention and application. As will be disclosed, the previously unknown and undisclosed 'best' AMH ranges of significance for this invention are similar regardless of the assay used.

What establishes outcome prognoses for infertile women entering IVF cycles is not well defined. That is, IVF cycles currently cannot be reliably prognosticated. The ability to reasonably predict prognoses would be, therefore, clinically valuable. It also would also enhance internal as well as external quality controls, the latter being mandated in the U.S. by an act of Congress and currently not satisfactorily accomplished.

Finally, treatments may demonstrate different levels of efficacy in good-, intermediate- and poor-prognosis patients. Better definition of "disease" severity, therefore, should improve individualization of IVF treatments.

Prognostication of IVF outcomes has been a longstanding goal. Various models have been published, with the key component being female age, as declining clinical pregnancy and live birth rates with advancing female age demonstrate. Therefore, changes in outcomes with advancing female age have to be considered when building prediction models for IVF.

Age is, however, not the only important predictor of IVF outcomes. Functional ovarian reserve (FOR), a term reflecting the growing follicle pool, and, therefore, oocyte and embryo numbers, is also closely associated with IVF outcomes. Abnormally low FOR (LFOR) is defined by abnormally increased age-specific follicle stimulating hormone (FSH) and/or decreased age-specific AMH, both reflecting declining egg and embryo numbers and, therefore, deteriorating pregnancy and live birth chances.

In women with premature ovarian aging (POA), also called occult primary ovarian insufficiency (oPOI), normal statistical associations between age and FOR are disturbed. POA/oPOI patients prematurely demonstrate LFOR. They, independent of race and ethnicity, represent approximately 10% of females and often more than half of all patients in IVF centers. FOR—rather than age-based models may, therefore, be preferable in POA patients.

Protocols for administration of AMH to women and girls have been proposed.

Average serum AMH is approximately 4 nanograms/milliliter (4 ng/ml) in healthy young women with normal ovarian reserve. Kelsey T W, Wright P, Nelson S M, Anderson R A, Wallace W H. A validated model of serum anti-mullerian hormone from conception to menopause. PloS one 2011; 6:e22024.

The half-life of AMH is 27.6 hrs. Griesinger G, Dafopoulos K, Buendgen N, Cascorbi I, Georgoulias P, Zavos A, Messini C I, Messinis I E. Elimination half-life of anti-Mullerian hormone. The Journal of clinical endocrinology and metabolism 2012; 97:2160-2163.

A time period of 90-120 days is the approximate time from primary follicle recruitment to ovulation. McGee E A, Hsueh A J. Initial and cyclic recruitment of ovarian follicles. Endocrine reviews 2000; 21:200-214

For women with low ovarian reserve who are pursuing controlled ovarian hyperstimulation (COH) for fertility treatment, there is a proposed protocol.

The proposed protocol is pretreatment with AMH prior to COH and is intended to improve follicular synchrony, oocyte yield and pregnancy rates with fertility treatments. Starting dose of AMH is 4 to 8 ng/ml daily.times.typical volume (5,500 ml)=22,000 to 44,000 ng/day for 90 days. The dose and duration may require adjustments based on future studies, patient size as well as other parameters. This treatment would be followed by a short washout period ranging from days to weeks. The short washout period would be followed by controlled ovarian hyperstimulation (commonly used agents include: gonadotropins, selective estrogen-receptor modulators, and aromatase inhibitors) and then followed by either Intrauterine Insemination or Oocyte Retrieval for In IVF or for Oocyte/Embryo cryopreservation.

For women and girls who are pursuing fertility preservation due to imminent exposure to gonadotoxic treatments, there is a further proposed protocol.

The further proposed protocol is treatment with AMH prior to and contemporaneously with gonadotoxic treatments and is intended to decrease activation and recruitment of primordial follicles via a so-called "burnout" effect, which induces rapid and often complete loss of ovarian reserve via follicle depletion. Recruitment adds follicles to the pool of so-called growing follicles, which, in contrast to primordial follicles, are very sensitive to damage from chemotherapy drugs and/or radiotherapy. Kalich-Philosoph L, Roness H, Carmely A, Fishel-Bartal M, Ligumsky M, Paglin S, Wolf I, Kanety H, Sredni B, Meirow D. Cyclophosphamide triggers follicle activation and "burnout"; AS101 prevents follicle loss and preserves fertility. Science translational medicine 2013; 5:185ra162.

By preventing follicle activation, AMH potentially protects the gonads from chemotherapy and radiation therapy by keeping follicles at primordial stages, where they are less sensitive to damage, thereby preventing loss of fertility as a consequence of gonadotoxic treatments, as currently seen in cancer patients and in other medical conditions requiring such treatments.

The starting dose of AMH is 4 to 8 ng/ml daily.times.typical adult volume (5,500 ml)=22,000 to 44,000 ng/day. Dose and duration may require adjustments based on future studies, patient size as well as other parameters. Lower doses may be appropriate for pediatric patients. Treatment with AMH is initiated several days prior to and continued during gonadotoxic treatment, AMH should be continued until gonadotoxic treatment is stopped.

There is a need to understand the affects of AMH levels on pregnancy rates, birth rates and miscarriage rates sufficient to administer AMH in a manner to control such rates. There is no basis in the prior art to control AMH at certain levels, as opposed to simply increasing AMH levels, in order to promote candidacy for IVF and/or to increase pregnancy, live birth and/or miscarriage rates. If such administration would be to achieve and/or maintain a certain AMH level, regardless of other hormones such as FSH and other treatments, an entirely new area of therapeutic utility for AMH would be disclosed and taught. This, in part, is the subject matter of this invention.

SUMMARY OF THE INVENTION

One aspect of the invention relates to the administration of AMH based on classification of patients at all ages prospectively as well as retrospectively into good-, intermediate- and poor prognosis for in vitro fertilization.

The classification arises by establishing, for all ages, definitions of good, intermediate and poor prognosis patients based on clinical pregnancy and live birth rates. Utilizing three, mostly overlapping patient cohorts, logistic regression models can be established with predictive of age-specific clinical and live birth rates based on three different functional ovarian reserve (FOR) parameters (good quality embryos, FSH and AMH).

Indeed, all three models at all ages allowed clear separations of good-, intermediate- and poor prognosis patients, though definitions change with age. In each age category, with transfer of similar embryo numbers, clinical pregnancy and live birth rates almost consistently improved with growing embryo production, although completely unaffected by embryo quality, as defined by pregnancy loss (i.e. mostly aneuploidy). While embryo and FSH models demonstrate almost linear associations with decreasing FSH and increasing embryo production, the AMH model demonstrates a bell-shaped polynomial pattern of association, with highest clinical pregnancy and live birth rates at mid-range. This "best" AMH level was associated with unexpectedly high clinical pregnancy and delivery rates in all age categories, reaching 17-18% clinical pregnancy even in women .gtoreq.43 years. The AMH model further suggested that AMH at "best" levels facilitates pregnancy and delivery chances but at excessive levels appears associated with increased miscarriage risk.

These findings are entirely new and, indeed, inconsistent with current teachings. For example, related art cited herein discloses higher AMH levels, or in one case administrating AMH to increase levels, can promote proper follicular development or other types of fertility treatment. The findings of this "best" AMH level and the risks associated with excessive AMH levels are unexpected and new. The findings allow new and useful therapy with AMH to promote pregnancy, live birth and/or miscarriage rates through achieving and/or maintaining specific levels in particular subjects.

Patients can be classified into good-, intermediate- and poor prognosis categories based on clinical pregnancy and live birth rates, using only age and FOR parameters. AMH, in addition, depending on concentration, independently, also appears to control pregnancy, delivery chances as well as pregnancy loss risk and, therefore, serves as a potential therapeutic agent.

Another aspect of the invention pertains to a method of diagnosing viability with in vitro fertilization. This method comprises ascertaining an AMH level of a subject from testing; and selecting one of a plurality of prognosis categories that applies to the ascertained AMH level by matching the ascertained AMH level with an applicable one of a plurality of ranges of AMH levels pertaining to an age of the subject. The plurality of prognosis categories are associated with specific of the plurality of ranges of AHM levels and is selected from the group consisting of good, intermediate and poor prognosis categories. The good prognosis category has a higher statistical chance of pregnancy success with the in vitro fertilization than that of the intermediate and poor prognosis categories. The poor prognosis category has a worse statistical chance of pregnancy success with the in vitro fertilization than that of the intermediate and good prognosis categories. The intermediate prognosis category has a statistical chance of pregnancy success with the in vitro fertilization that is between that for the poor and good prognosis categories.

Yet another aspect of the invention relates to a method for terminating pregnancy or increasing miscarriage rate in a subject, comprising administering to the subject an effective amount of AMH to achieve and maintain an AMH level that is higher than that of (i) 7.0 ng/ml for the subject being under 36 years old, and (ii) 6.5 ng/ml for the subject being 36-42 years old inclusive.

Still another aspect of the invention relates to a method for decreasing a pregnancy rate in a subject, comprising administering to the subject an effective amount of AMH to achieve and maintain an AMH level that is higher than that of (i) 8.5 ng/ml for the subject being under 36 years old; (ii) 7.5 ng/ml for the subject being 36-38 years old inclusive; (iii) 7.0 ng/ml for the subject being 39-42 years old inclusive; and (iv) 7.5 ng/ml for the subject being over 42 years old.

BRIEF DESCRIPTION OF THE DRAWING

For a better understanding of the present invention, reference is made to the following description that pertains to the drawings set forth in U.S. utility patent application Ser. No. 15/015,543, whose drawing contents are incorporated by referent pertaining to FIG. 1A, FIG. 1B, FIG. 1C, FIG. 1D, FIG. 2A, FIG. 2B, FIG. 2C, FIG. 2D, FIG. 3A, FIG. 3B, FIG. 3C and FIG. 3D, while the scope of the invention is set forth in the appended claims.

FIG. 3B is pregnancy probability graph based on the content of the chart of FIG. 3a.

DESCRIPTION OF THE PREFERRED EMBODIMENTS

The present invention is based on our study that was initiated to determine whether, even in a relatively adversely selected infertile patient population, definitions of good-, intermediate- and poor prognosis can still be made in different age categories. Such information would obviously be prospectively useful to patients planning to undergo IVF but, even retrospectively, would also allow for better definitions of patient populations undergoing IVF and, therefore, for better outcome comparisons between centers. In the U.S., where, to allow for such comparisons, national outcome reporting is legislatively mandated by Congress, the current system has recently been demonstrated to be inadequate and even misleading. Yet another reason for this study was the recent recognition that effects of various IVF treatments greatly vary between good-, intermediate- and poor-prognosis patients, and, indeed, may be outright harmful in the latter group.

This study, therefore, approached the issue differently than conventional approaches by primarily assessing the impact of FOR on IVF outcome in three distinctively different models: In a retroactive model, based on number of embryos produced in a given IVF cycle, and in two prospective models, utilizing FOR's two most widely used laboratory surrogates, FSH and AMH. While the prospective definition of prognosis of IVF patients has been a longstanding goal in the field with various conventional models proposed, it is our assessment that none of those various conventional models have been proven clinically effective so far.

Patient Populations

This study involves three partially overlapping patient cohorts: Cohort I, 1,247 consecutive fresh IVF cycles during 2009-2013, including egg donor cycles, however excluding elective single embryo transfer (eSET) and mild stimulation cycles, was used to investigate associations of good quality embryo numbers (1-15) with clinical pregnancy and live birth rates at different ages (<36, 36-38, 39-40, 41-42 and .gtoreq.43 years). Patients <36 are presented as a single age category because ages <30, 31-32, 33-34 and 35-36 produced basically identical outcomes as graphed in FIGS. 1a-1d.

Cohort II, 1514 consecutive fresh autologous non-donor IVF cycles, excluding eSET and mild stimulation cycles, was used to establish associations of highest FSH levels (2.5-40.0 mIU/ml) with clinical pregnancy and live birth rates, stratified for age.

Cohort III, 632 fresh autologous non-donor cycles between 2011-2014, excluding eSET and mild stimulation cycles, was used to assess associations of lowest AMH levels (<0.5-10.0 ng/ml) with clinical pregnancy and live birth rates, stratified for age. Only AMH measurements by the Beckman Generation 2 AMH assay were included.

All patient data were extracted from our center's anonymized electronic research data base, representing consecutive IVF cycles, unless meeting exclusion criteria noted above. Table 1 summarizes patient and IVF cycle characteristics for all three patient cohorts.

FSH and AMH Values

FSH values were ascertained in house by commercial assay. Again, as stated above, laboratory test procedures and equipment to ascertain an AMH level are conventionally known. For this study, AMH was assessed with such Generation II (second generation) assays. Those skilled in the art will understand that other generations of assays and conventional test procedures could be used as well. Since earlier generation AMH assays deviate from the here utilized assay, values reported in this study cannot be applied to other AMH assays at the very high or very low ranges; however, in mid-range, all AMH assays are very similar. As later demonstrated, mid-range values mattered most in this study. While AMH assays may vary at the extremes of very high or very low AMH levels, they are very similar in the medium and other ranges significant for this invention and application.

IVF Cycle Protocols

Cycle stimulation protocols at our center are limited, and choice of gonadotropin manufacturer is deferred to patients and their medical insurances. Oocyte donors receive a long agonist protocol (150-300 IU of gonadotropins daily), usually given as human menopausal gonadotropin (hMG). Since most of our center's patients present with LFOR, a majority receive short microdose agonist protocols, with FSH (300-450 IU) and hMG (150 IU). Patients with normal FOR, if under age 38, receive similar stimulation as to egg donors. Patients with LFOR are pretreated with dehydroepiandrosterone (DHEA) to raise testosterone levels to above 28 ng/ml (1nmol/L) before IVF cycle start, 18 and also receive CoQ10 supplementation. 19 Up to age 38, our center transfers in fresh cycles only 1-2 embryos; between ages 38-42, 3 embryos and above age 42, 3 to maximally 5 embryos.

Embryo Assessment

Our center routinely transfers embryos on day-3 (cleavage stage) after assessment and grading. 20 Only 4-8-cell embryos on day-3 of at least grade 3 are transferred or cryopreserved and, therefore, considered good quality.

Statistics

FOR parameters and categorical age were used to model the probability of clinical pregnancy, live birth or pregnancy loss using logistic regression. For models with AMH, AMH2 was also included, and a statistically significant predictor of all outcomes. A P-value of <0.05 was considered statistically significant. All statistical analyses were preformed using SAS version 9.4 software.

Results

Effects of Embryo Numbers

Table 2 summarizes cycle characteristics for Cohort I. As expected, good quality embryos, pregnancy and live birth rates declined with advancing age, while miscarriage rates increased.

How embryo numbers affected clinical pregnancy and live birth rates is shown in FIGS. 1a-1d: Good-, intermediate- and poor outcomes within each age category were defined at break points of pregnancy and live birth rates. In all figures, fields were colored in yellow for poor prognosis, in blue for good prognosis and left uncolored for intermediate-prognosis.

Figure 1A:
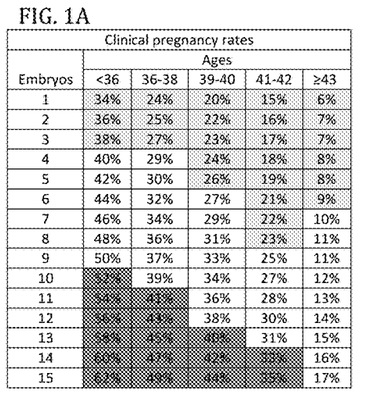
FIG. 1A is a chart showing age-specific model of pregnancies based on good quality embryos produced per cycle for clinical pregnancy rates.
Figure 1B:
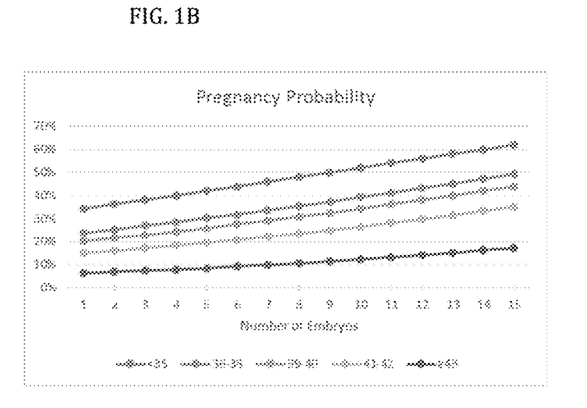
FIG. 1B is pregnancy probability graph based on the content of the chart of FIG. 1A.
Figure 1C:
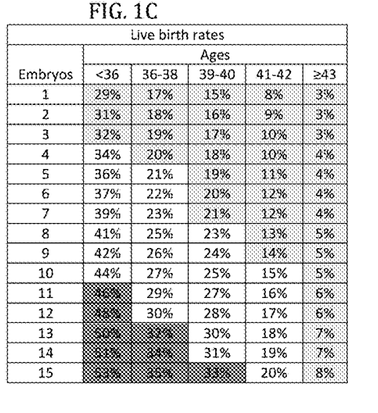
FIG. 1C is a chart showing age-specific model of live births based on good quality embryos produced per cycle for live birth rates.

As FIGS. 1a and 1c demonstrate, at youngest age (<36 years) pregnancy and delivery rates were excellent almost independent of good quality embryo numbers. Even poor prognosis patients (defined by only 1-3 embryos) still achieved clinical pregnancy rates of 34-38% and live birth rates of 29-32%. Both rates steadily increased with increasing embryo production to a maximum of 62% and 53%, respectively.

Because our center only rarely performs eSET, 21 and up to age 38 practically never transfers more than 2 embryos, this age category at most received 2-embryo transfers (2 ETs). Yet, pregnancy and live birth rates increased almost linearly (FIGS. 1b and 1d) with increasing embryo production.

The pregnancy loss rate, defined as clinical pregnancies minus live births, however remained similar, whether a woman produced 1 or 15 embryos: Pregnancy loss <36 occurred in 14.7% of women with 1 embryo and in 14.5% of women with 15 embryos.

FIGS. 1a and 1c also demonstrate that, despite uniformly good clinical pregnancy and live birth rates <36 years, separation of good-prognosis (gtoreq.51% clinical pregnancy and .gtoreq.44% live birth), intermediate prognosis (respectively 40-50% and 34-44%) and poor prognosis patients (respectively <39% and <33%) was still possible.

Figure 1D:
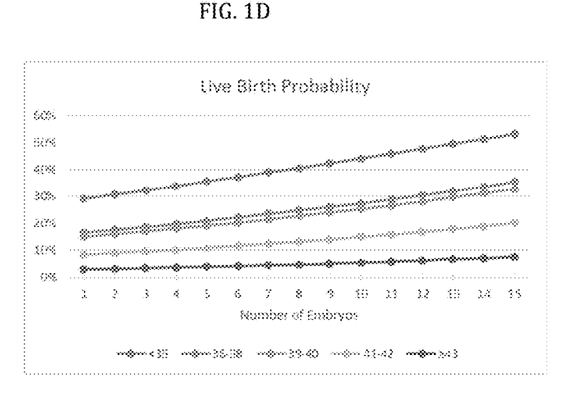
FIG. 1D is a live birth probability graph based on the content of the chart of FIG. 1C.

From age 36, outcomes started declining, while pregnancy losses increased, at age 36-38 reaching 29.2% for women who produced 1 and 28.6% in those with 15 embryos. This traditional embryo quality parameter, thus, remained stable (FIGS. 1a and 1c) and almost linear improvements of pregnancy and live birth rates with increasing embryo production was maintained into older ages (FIGS. 1b and 1d). Indeed, improvements within age categories between 1 and 15 embryos grew with advancing age: Under age 36, clinical pregnancy chances increased by 82.4% (from 34% to 62%) but by 104.2% (from 24% to 49%) in age category 36-38. Concomitantly, live birth rates improved by 89.3% (from 29% to 53%) under age 36 and by 105.9% (from 17% to 35%) at ages 36-38. By age .gtoreq.43, clinical pregnancy rate for 1 embryo was 6%, and for 15 embryos 17%, a 183% increase, while live births increased from 3% to 8%, a 166.7% increase (FIG. 1).

As FIGS. 1a and 1c demonstrate, with persistently decreasing clinical pregnancy and live birth rates, women .gtoreq.43 years only with 7 or more embryos reached 10% clinical pregnancy rates or higher, and even with up to 15 embryos remained in single digit range for live births. No woman in that age group, therefore, could be considered a good prognosis patient.

Increasingly, poor embryo quality with advancing female age was also reflected in increasing pregnancy loss, in women with 1 embryo reaching 50.0% at age .gtoreq.43, and 52.9% with 15 embryos. The embryo quality parameter of pregnancy loss, therefore, remained similar within age categories,—even at most advanced age; yet, clinical pregnancy and live birth rates within age categories improved with growing embryo numbers produced, and did so more and more as women aged.

Even though embryo numbers transferred were similar within age categories, pregnancy and live birth rates in each age category almost linearly increased between 1-15 embryos with increasing embryo production. Concomitantly, pregnancy loss rates, defined as clinical pregnancies minus live births, remained similar within age categories in embryo and FSH models, whether a woman produced 1 or 15 embryos. In the AMH model, pregnancy loss also remained stable within age categories at low and intermediate ("best") AMH levels but spiked in all age categories at highest AMH levels.

Embryo quality has been strongly associated with pregnancy loss rates because embryo aneuploidy is considered the by far most frequent cause of miscarriages. The whole concept of pre-implantation genetic diagnosis (PGS) is, indeed, based on this association and the consequential step of attempting to eliminate aneuploid embryos prior to embryo transfer.

Our study, therefore, demonstrated that this aneuploidy-associated definition of embryo quality did not change with increasing embryo production within age categories, except at very high AMH levels; yet, increasing embryo production, independent of numbers of embryos transferred, still was strongly associated with improving clinical pregnancy and live birth rates.

This previously unknown association, thus, establishes an additional, previously unknown embryo quality parameter, in itself strongly associated with increasing embryo numbers and, therefore, with improving FOR.

The study also demonstrated that, again somewhat surprisingly, only at age 36 years outcomes started to decline with advancing age. Concomitantly, pregnancy loss also increased in parallel, reaching at least 50% by age .gtoreq.43 years. Yet, within all age categories pregnancy loss remained the same independent of embryo numbers produced by patients, except in the AMH model, where pregnancy loss spiked at highest AMH levels. In addition, at all ages relative IVF outcome improvements between 1 and 15 embryos actually expanded with advancing age.

This newly discovered embryo quality parameter, described above, thus, appears to gain in physiologic importance with advancing age.

Effects of FSH Levels

Table 2 describes cycle numbers, peak FSH levels and clinical pregnancy as well as live birth rates at different female ages.

FIGS. 2a-2d summarize probabilities of clinical pregnancies (FIGS. 2a and 2b) and live births (FIGS. 2c and 2d) at FSH levels between 2.5-40.0 mIU/ml: Both at all ages declined with increasing FSH levels. Moreover, within each FSH category, both outcomes also declined with advancing age. In all figures, fields were colored in yellow for poor prognosis, in blue for good prognosis and left uncolored for intermediate-prognosis.

For women <36 years, FSH only up to 7.5 mIU/ml denoted good prognosis (pregnancy 36-43%; live birth 30-36%). FSH levels mattered at all ages, with lower FSH levels, even with good-prognosis and within normal FSH levels offering better outcomes. Pregnancy after age 40, and live births even as early as age 36, failed to reach good-prognosis at even lowest FSH, suggesting that, at least in adversely selected patients, normal FSH levels may have to be reconsidered.

Figure 2A:
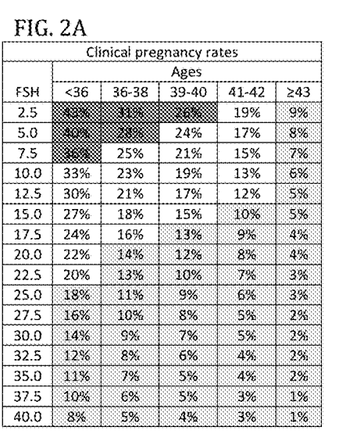
FIG. 2A is a chart showing age-specific model of pregnancies based on FSH levels (in mIU/ml) for clinical pregnancy rates.
Figure 2B:
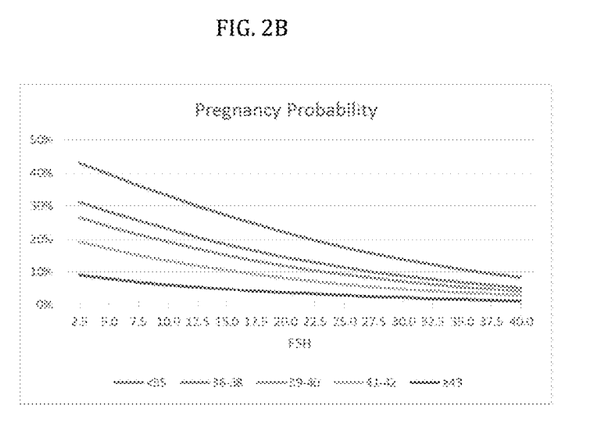
FIG. 2B is pregnancy probability graph based on the content of the chart of FIG. 2A.
Figure 2C:
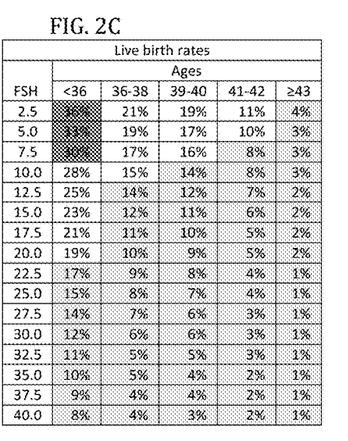
FIG. 2C is a chart showing age-specific model of live births based on FSH levels (in mIU/ml) for live birth rates.
Figure 2D:
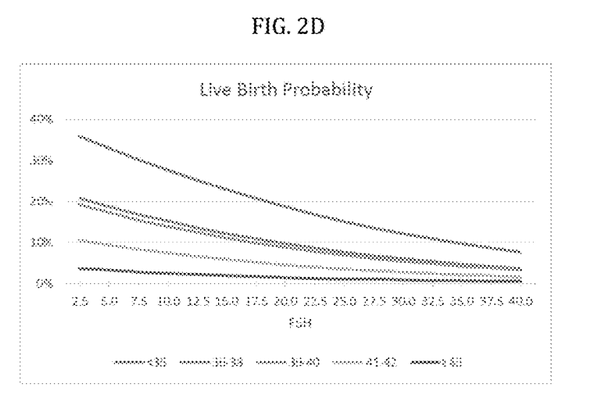
FIG. 2D is a live birth probability graph based on the content of the chart of FIG. 2C.

FSH changed in its clinical relevance with advancing female age: For example, an FSH of 22.5-25.0 mIU/ml<36 years resulted in clinical pregnancy in 19%; though at age 41-42, the same rate required an FSH of 2.5 mIU/ml (FIG. 2a); FSH of 32.5 mIU/ml<36 years, allowed live births in 11%; but at 41-42, this live birth rate required an FSH of 2.5 mIU/ml (FIG. 2c).

FIGS. 2a-2d also demonstrate that .gtoreq.43 years treatment futility, according to the American Society for Reproductive Medicine (ASRM) at ca. 1 live birth rate, 22 was reached at FSH 22.5 mIU/ml. Yet, up to 42 years, even up to FSH 40.0 mIU/ml futility was avoided.

Observed FSH dynamics, in contrast, did not surprise: as expected, with increasing FSH levels clinical pregnancy and live birth rates declined at all ages. Moreover, the same was true with advancing age within each FSH category. FSH levels, thus, mattered at all ages, with lower FSH levels, even within what is widely perceived a normal FSH range, offering better outcomes. These data reemphasize the importance of assessing patients with age-specific FSH levels.

Effects of AMH Levels

Figure 3A:
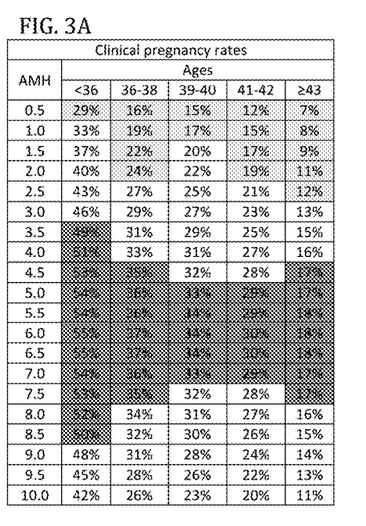
FIG. 3A is a chart showing age-specific model of pregnancies based on AMH levels (in ng/ml) for clinical pregnancy rates.
Figure 3B:
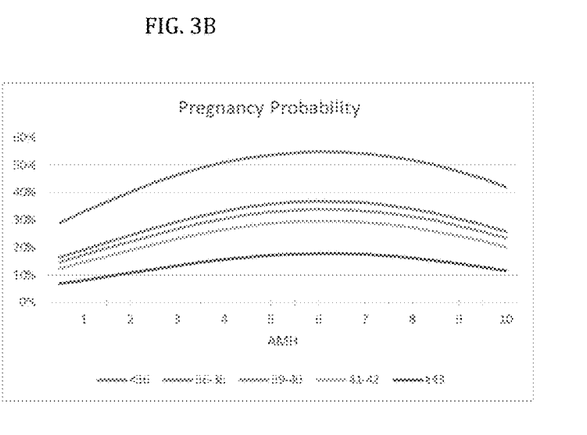
Figure 3C:
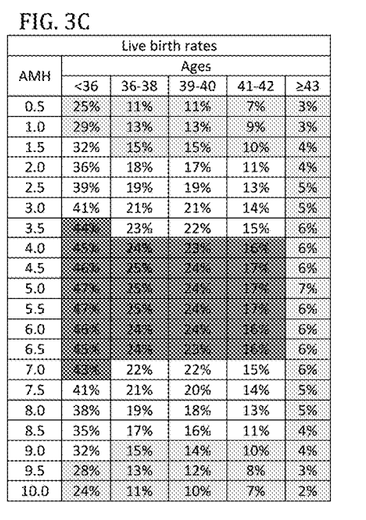
FIG. 3C is a chart showing age-specific model of live births based on AMH levels (in ng/ml) for live birth rates.
Figure 3D:
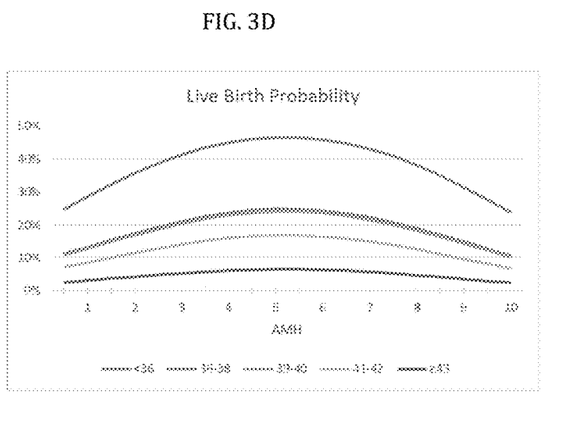
FIG. 3D is a live birth probability graph based on the content of the chart of FIG. 3C.

Table 2 also introduces Cohort III, which was used to assess associations of lowest AMH (between >0.5 ng/ml and 10.0 ng/ml) with pregnancy (FIGS. 3a and 3b) and live birth rates (FIGS. 3c and 3d). In contrast to embryo and FSH models, pregnancy and live birth chances in association with AMH followed a bell-shaped curve, with best outcomes at midrange.

The very high pregnancy and live birth rates at "best" AMH levels were unexpected: Under age 36, AMH values between 3.5 ng/ml and 8.5 ng/ml offered best pregnancy chances (49-55%, good-prognosis patients); 1.0-3.0 ng/ml, and 9.0-10.0 ng/ml offered intermediate-prognoses (pregnancy 33-46%), and only AMH 0.5 ng/ml poor prognosis (pregnancy rate of 29%, FIG. 3a).

Live births behaved similarly: Best live birth rates (43-47%) were obtained at AMH 3.5-7.0 ng/ml; intermediate rates (32-41%) at AMH of 1.5-3.0 ng/ml and 7.5-9.0 ng/ml. Even poor prognosis at AMH of 1.0 ng/ml still was associated with 25-29% live births.

Clinical pregnancy and live birth declined only mildly up to age 42, and an unexpectedly high 18% pregnancy rate was still achieved .gtoreq.43. Live births reached a respectable 7% (oldest conception at age 47). Pregnancies in single digits occurred only with AMH <1.5 ng/ml. With AMH >2.0 ng/ml, clinical pregnancy rates were between 10-18%, though declined at very high AMH (FIG. 3a) after reaching peak pregnancy rates at AMH 5.5-6.5 ng/ml. This patient group, however, also experienced the highest pregnancy loss rate of any model.

Pregnancy loss at all ages remained similar for low and "best" AMH levels but significantly increased at highest AMH levels: <36 years, at AMH 0.5 ng/ml only 13.8% miscarried and at "best" level of 5.5 ng/ml only 13.0%; but at AMH of 10.0 ng/ml, rates spiked to 42.9%. The same occurred .gtoreq.43, where pregnancy loss was 57.1% with lowest AMH, 61.1% at "best" AMH levels and spiked to 81.8% at highest AMH, contradicting that AMH linearly reflects not only oocyte quantity but also quality. 23

The most consequential findings of this study, however, relate to AMH levels: While in embryo and FSH models relationships were almost linear, clinical pregnancy and live birth chances in relation to AMH levels followed a bell-shaped curve, with maximal clinical pregnancy and live birth chances at midrange AMH, rather than at highest or lowest levels.

This model, indeed, demonstrated unexpectedly high pregnancy rates at "best" AMH levels even into oldest age categories. Live birth rates behaved similarly and were up to age 42 remarkably high. Even at "best" AMH levels, beyond age 42 extremely high rates of pregnancy loss were, however, observed. Women .gtoreq.43, at "best" AMH levels, for example, reached an almost incredulous 18% clinical pregnancy rate but only a 7% live birth rate, representing a 61.1% clinical miscarriage rate. While a live birth rate of 7% in this age category has still to be considered remarkable, the rate of observed pregnancy loss is even more so.

While in embryo and FSH models pregnancy loss rates remained the same within age categories independent of embryo numbers and FSH levels, we noted earlier that in the AMH model in all age categories miscarriage rates only remained similar at low and "best" AMH levels but spiked significantly at highest AMH levels. In the oldest age category .gtoreq.43 years, pregnancy loss reached 57.1% in women with 1 embryo, 61.1% at "best" AMH levels and, indeed, spiked to 81.8% at highest AMH levels.

Combined, all of these findings strongly suggest favorable AMH-associated effects on clinical pregnancy in association with IVF especially at good and "best" AMH levels, and unfavorable effects in association with increasing miscarriages with highest AMH levels. These observations, therefore, contradict the widely expressed belief that AMH values linearly reflect not only oocyte quantity but also quality Statistical Comments Because all three here utilized statistical models highly correlate in representation of FOR in association with patient age, construction of combined statistical models was not feasible. In univariate models, FSH and AMH, independently, were not predictive of miscarriage. Embryo numbers, however, did reach significance in an univariate model (P=0.008), though, as expected, significance was lost with adjustments for age, as embryo numbers in themselves are age-dependent. Table 1. Patient characteristics of patient Cohorts I, II and III Findings This study was initiated to determine whether it was possible in a somewhat adversely selected infertile patient population to reach definitions of good-intermediate- and poor prognosis in different age categories based on clinical pregnancy and live birth rates. Surprisingly, age-specific investigations of clinical pregnancy and live birth rates in IVF via here presented three distinct outcome models revealed previously unknown insights into physiological processes that favor clinical pregnancy chances and miscarriage risk in association with IVF.

As expected, defining parameters for individual prognosis categories changed with advancing female age, and required increasing embryo numbers to maintain designations. With clinical pregnancy as final outcome, women .gtoreq.43 years no longer demonstrated what could be defined as good prognoses. With live birth as final outcome, all women in that age category demonstrated, indeed, poor prognosis.

Utilizing peak FSH levels as FOR surrogate, similar associations became apparent (FIG. 2): Pregnancy and live birth rates declined with increasing FSH and advancing age. Again, prognoses could be defined based on cut offs in pregnancy and live birth rates. This model, however, already at young ages revealed a surprisingly narrow range of good-prognosis: In women <36 years, only FSH <7.5 mIUmL, and at ages 36-37, only FSH <2.5 mIU/ml qualified with reference point pregnancy as good-prognosis, while with end point live birth, only age <36 qualified. Even intermediate-prognosis became rare after age 40, and required FSH levels <5.0 mIU/ml, while only poor-prognosis patients were left .gtoreq.43 years.

These data confirm the importance of utilization age-specific FSH levels in assessing infertile women.

Somewhat surprising observations were made in the AMH model: In contrast to the two previously discussed embryo and FSH models, it demonstrated a typical bell-shaped polynomial pattern. In all figures, fields were colored in yellow for poor prognosis, in blue for good prognosis and left uncolored for intermediate-prognosis. Worst IVF outcomes were observed at AMH extremes; "best" AMH was slightly above mid-point (FIGS. 3a-d). In pregnancy rates this pattern carried over into the oldest patient category (FIG. 3a), though based on live births, no good prognosis patients were found .gtoreq.43 years (FIG. 3c).

Here reported outcomes are, of course, not automatically applicable to other IVF programs. They were results of very specific practice patterns. 18, 25 Even assuming identical patient populations (in itself also a highly unlikely proposition), different clinical protocols at other centers will result in different pregnancy and live birth rates. To construct universally applicable models, this study will have to be repeated on a multicenter or even national basis, and further validated against results from IVF centers with varying patient populations and treatment protocols.

Different AMH assays utilized by IVF centers may also offer mildly varying results, 26 though mid-range AMH, in this study demonstrated to be most important AMH range, demonstrates least discrepancies between currently used AMH assays.

Relevance of Treatment Protocols

Reliable prognostication of patients is of potential clinical importance: Treatments, which recently entered routine IVF, have shown varying effectiveness in different patient categories. For example, the concept of embryo selection in all of its applications appears beneficial only in good-prognosis patients. With intermediate-prognosis, embryo selection appears ineffective, while with poor prognosis it outright decreases pregnancy and live birth chances. 4 At the other extreme, treatments reported effective in adversely selected patients 18, 19, 25 may be ineffective in intermediate and good prognosis patients.

IVF protocols, therefore, have to evolve toward individualization of care, and a reproducible classification of patients, as here presented, would greatly contribute to standardization of individualized treatment options.

Unanticipated Finding

An unanticipated finding from the study concerns a previously unknown embryo quality parameter, apparently closely associated with AMH. The parameter appears to increase in physiologic importance with advancing female age. This finding raises the possibility of using AMH as a potential therapeutic drug in affecting infertility treatment outcomes.

The most unexpected findings of this study were counterintuitive, and in some aspects contradictive to currently prevailing opinions. For example, current consensus holds that egg/embryo quantity and quality run in parallel; as quantity declines with advancing age, so does quality.

Assuming this to be correct, one would expect declining embryo quality within age categories, with best pregnancy rates occurring in women with highest embryo production. With clinical pregnancy and live birth rates in every age category increasing in parallel with increasing embryo numbers, this, indeed, on first glance appeared to be the case. Closer analysis, however, revealed that observed outcome improvements, likely, did not reflect improving traditional embryo quality since in each age category the rate of spontaneous pregnancy loss (i.e., the difference between clinical pregnancy and live birth rates) remained constant,— whether a patient produced 1 or 15 embryos. What has been traditionally perceived as a major component of embryo quality, therefore, apparently does not change with increasing embryo production.

Yet, as expected, pregnancy loss rates, reflecting this traditionally embryo quality parameter, still did increase with advancing age categories.

The embryo's chromosomal constitution, widely accepted as a principal indicator of traditional embryo quality, and the theoretical basis of PGS1, therefore, does not appear involved in the observed IVF outcome improvements within age categories with increasing embryo numbers. The question, therefore, is what drives this new observation?

It obviously has to be another, non-chromosomal component of embryo quality, which, based on here presented data, increases with increasing embryo numbers. In trying to ascertain potential associations, we considered the possibility that co-culture of multiple embryos may have beneficial effects on implantation but dismissed this explanation since our laboratory at most co-cultures only three to four embryos in one dish. Co-culture of embryos, therefore, could not explain the almost linear increase in clinical pregnancy and live birth rates up to 15 embryos within age categories.

FOR, thus, appears defined by more than just age since quantity of oocytes/embryos, in themselves, appears to reflect the embryos' ability to implant and lead to clinical pregnancy, independent of traditional embryo quality parameters, like aneuploidy.

This, in itself, is a potentially important finding, and may, at least partially explain why the concentration on ploidy in defining embryo quality through utilization of the PGS procedure has so far failed to improve IVF outcomes contrary to most predictions. 6,7

Here presented data suggest that a major second factor affects embryo quality, and with advancing age assumes increasing importance for the establishment of pregnancy in association with IVF.

This second factor is, of course, still unknown but lends itself to speculations: It must be associated with increasing oocyte/embryo production in IVF cycles; yet, since observed improvements with increasing embryo numbers almost doubled between youngest and oldest age categories, its efficacy must increase with advancing female age.

AMH is, of course, strongly associated with oocyte/embryo production in IVF. At "best" AMH levels, our third model demonstrated extraordinarily high clinical pregnancy rates into even the oldest age categories. Women at ages 41-42 years achieved clinical pregnancy rates of 29-30%, and of 17-18% even at ages 43 and above. Neither embryo nor FSH models, however, demonstrated such extraordinary clinical outcomes at advanced age categories.

One, therefore, can further hypothesize that these extraordinary outcomes relate to "best" AMH levels, which in this study were defined at ranges of 3.5-8.5 ng/ml in the youngest, and in a somewhat narrower range between 4.5-7.5 ng/ml in the oldest age categories. Even oldest women with AMH in "best" range still experienced extraordinarily high clinical pregnancy chances of 17-18%.

Yet, this apparently beneficial AMH-associated effect on clinical pregnancy rates was mostly lost to high miscarriage rates and, therefore not reflected in equally high live birth rates. While live birth rates remained relatively high until age 42, at or above age 43, live birth rates at "best" AMH levels, though still higher (6-7%) than at very low or very high AMH levels (2-5%), had lost significant ground.

Combined, these observations, however, support the very interesting hypothesis that AMH effects on clinical IVF outcomes are dosage-dependent: At all ages, AMH at "best" levels (or an AMH-associated factor) improved the ability of embryos to implant, leading to quite extraordinarily high clinical pregnancy rates. Whether this represents an AMH effect on oocytes, embryos or the endometrium remains to be determined.

At very high levels, AMH, however, is also associated with increased pregnancy loss. This conclusion is supported by the here reported observation that pregnancy loss in all age categories spikes at very high AMH levels, in the oldest age category .gtoreq.43 years reaching as high as 81.8%, while at low and "best" levels being only around 60% even in this oldest patient category.

Here reported observations, therefore, support the hypothesis that AMH (or an AMH-associated factor) plays an undefined favorable modulatory role at "best" levels in establishing pregnancies in association with IVF. Excessively high levels, however, lead to pregnancy loss. The relative importance of this AMH-associated effects increases with advancing female age, which may suggest a potential therapeutic role for AMH at appropriate dosages in improving clinical outcomes in IVF, especially in older women.

Preferably, the protocol for manufacturing recombinant AMH or purifying it is in the TGF-beta superfamily and there are other compounds in this family that have been manufactured for human use. Also there are several companies that manufacture it for research purposes, as exemplified below, but no one that makes it for human use yet.

The protocol may be expressed in CHO cells prior to human use. CHO cells are a laboratory-cultured cell line derived from cells from the ovaries of Chinese hamsters. Chinese hamsters are a popular laboratory mammal, partially due to their small size and low chromosome number, which makes them a good model for tissue culture and radiation studies. They are a commonly-used mammalian cell model used in biology and in medical and pharmaceutical research. In addition, they are frequently used for commercial purposes to manufacture therapeutic recombinant proteins.

R&D Systems—Recombinant Human MIS/AMH Protein www.rndsystems.com/products/recombinant-human-mis-amh-protein 1737-ms OriGene—AMH (NM 000479) Purified Human Protein, Catalog # TP308397 www.origene.com/protein/TP308397.aspx abm—AMH Recombinant Protein www.abmgood.com/AMH-Recombinant-Protein-AMH.html MyBiosource—AMH recombinant protein: Anti-Mullerian Hormone (AMH) Recombinant Protein, Catalog # MB 52010947 www.mybiosource.com/prods/Recombinant-Protein/Anti-Mullerian-Hormo-ne-AMH/AMH/datasheet.php-?products_id=2010947

The contents of U.S. provisional patent application No. 62/128,127 are incorporated herein by reference as concerns the contents under the Description on pages 18-65, inclusive in particular of the discussion under the heading "Compositions" on page 21, "Peptides" on pages 21-30, "Nucleic Acids and Vectors" on pages 31-40, "Treatment Methods" on pages 40-43, "Pharmaceutical Compositions and Formulations" on pages 43-56, "Administration/Dosing" on pages 56-61, "Routes of Administration" on pages 61-65, and "Vaginal Administration" on pages 65-66. The manufacture of a composition containing AMH that is described is applicable for use with the present invention and its delivery method and dosages are applicable as well, except that the amount administered over time in accordance with the invention varies, dependent upon the age of the subject, in a manner that either: [0132] achieves and maintains the patient AMH level within confines of the probability bell curves of FIG. 3A or FIG. 3C as applicable to increase the probability, or [0133] achieves and maintains the patient AMH level outside confines of the probability bell curves of FIG. 3A or FIG. 3C as applicable to decrease the probability.

The confines of the bell curve of FIG. 3B pertain to pregnancy probability of the subject and the confines of the bell curve of FIG. 3D pertain to live birth probability of the subject. The bell curves represent statistical chance of success for pregnancy in the case of FIG. 3B as tabulated in FIG. 3A and the statistical chance for success of live birth in the case of FIG. 3D as tabulated in FIG. 3C.

The AMH levels for good, intermediate and poor pregnancy probability are in FIG. 3B (set forth as AMH level ranges for subject age ranges) and for good, intermediate and poor live birth probability are in FIG. 3C (set forth as AMH level ranges for subject age ranges). The AMH levels of FIGS. 3A and 3C are readily entered, stored and categorized in machine readable media, such as a computer memory, into different ranges of AMH levels corresponding to either good, intermediate or poor prognosis categories with respect to being a viable candidate for in vitro fertilization for the different age ranges.

In this application, the concept of categorizing ranges of AMH levels into good, intermediate and poor prognosis categories according to subject age is intended to encompass either display of any of FIGS. 3A-3D (that indicate the categories) or accessing from computer memory stored AMH level data from any of FIGS. 3A-3D in a manner that categorizes the stored data into the prognosis categories.

The AMH level for a subject can be ascertained through conventional testing. Once the AMH level is known, it is a simple matter to match the age of the subject with the applicable one of the different age ranges for which the AMH levels are categorized and to match the ascertained AMH level with an applicable one of the ranges of AMH levels that correspond to the good, intermediate and poor prognosis categories. Such matching can be used to determine whether the subject is viable as a candidate for in vitro fertilization with respect to pregnancy probability, live birth probability or both.

The bell curve of FIG. 3B in view of the tabulated AMH levels set forth in FIG. 3A indicates categories, which pertain to the viability of a candidate for in vitro fertilization with respect to pregnancy probability, namely, a good prognosis group, an intermediate prognosis category and a poor prognosis group.

The good prognosis category that pertains to pregnancy probability is in accord with AMH level ranges of only:

3.5 to 8.5 ng/ml inclusive encompassing the ascertained AMH level for the subject that is under 36 years old, 4.5 to 7.5 ng/ml inclusive encompassing the ascertained AMH level for the subject that is 36 to 38 years old inclusive, 5.0 to 7.0 ng/ml inclusive encompassing the ascertained AMH level for the subject that is 39 to 42 years old inclusive, and 4.5 to 7.5 ng/ml inclusive encompassing the ascertained AMH level for the subject that is over 42 years old.

The intermediate prognosis category that pertains to pregnancy probability is in accord with any of AMH level ranges of only:

1.0 to 3.0 ng/ml inclusive and 9.0 to 10.0 ng/ml inclusive encompassing the ascertained AMH level for the subject that is under 36 years old, 2.5 to 4.0 ng/ml inclusive and 8.0 to 10.0 ng/ml inclusive encompassing the ascertained AMH level for the subject that is 36 to 38 years old inclusive, 1.5 to 4.5 ng/ml inclusive and 7.5 to 10.0 ng/ml inclusive encompassing the ascertained AMH level for the subject that is 39 to 40 years old inclusive, 2.5 to 4.5 ng/ml inclusive and 7.5 to 10.0 ng/ml encompassing the ascertained AMH level for the subject that is 41 to 42 years old inclusive, and 3.0 to 4.0 ng/ml inclusive and 8.0 to 10.0 ng/ml inclusive encompassing the ascertained AMH level for the subject that is over 42 years old.

The poor prognosis category that pertains to pregnancy probability is in accord with AMH level ranges of only:

0.0 to 0.5 ng/ml inclusive encompassing the ascertained AMH level for the subject that is under 36 years old, 0.0 to 2.0 ng/ml inclusive encompassing the ascertained AMH level for the subject that is 36 to 38 years old inclusive, 0.0 to 1.0 ng/ml inclusive encompassing the ascertained AMH level for the subject that is 39 to 40 years old inclusive, 0.0 to 2.0 ng/ml inclusive encompassing the ascertained AMH level for the subject that is 41 to 42 years old inclusive, 0.0 to 2.5 ng/ml inclusive encompassing the ascertained AMH level for the subject that is over 42 years old.

Based on FIGS. 3C and 3D, one can observe that the good prognosis category for live birth probability arises in accord with:

5.0-6.5 ng/ml inclusive for the subject who is between 39-42 years old, 4.5-6.5 ng/ml inclusive for the subject who is between 36-28 years old, and 3.5-7.0 ng/ml for the subject who is under 36 years old.

However, after comparing FIGS. 3A and 3B with FIGS. 3B and 3D, one can recognize the full extent of AMH levels in each of the good, intermediate, poor prognosis groups are not the same as between clinical pregnancy rates and pregnancy probability versus live birth rates and live birth probability. That is, some of the AMH levels overlap and some do not for each of the good, intermediate and poor categories.

One can identify the AMH levels that overlap each other for the good prognosis categories for both pregnancy probability and live birth probability. The non-overlapping portions that were considered good prognosis for one or the other can be considered instead as intermediate prognosis for both. One can also identify the AMH levels that overlap each other for the intermediate prognosis categories for both pregnancy probability and live birth probability. The non-overlapping portions that were considered intermediate prognosis for one or the other can be considered instead poor prognosis for both. The following identifies specific values from the AMH level ranges obtained from a conventional Generation II (second generation) assay, but similar values of AMH, obtained by other AMH assays, are encompassed by the present invention.

The good prognosis category pertains to both pregnancy probability and live birth probability and is in accord with AMH level ranges of:

3.5 to 7.0 ng/ml inclusive encompassing the ascertained AMH level for the subject that is under 36 years old, 4.5 to 6.5 ng/ml inclusive encompassing the ascertained AMH level for the subject that is 36 to 38 years old inclusive, and 5.0 to 6.5 ng/ml inclusive encompassing the ascertained AMH level for the subject that is 39 to 42 years old inclusive.

Also, the intermediate prognosis category pertains to both pregnancy probability and live birth probability and is in accord with AMH level ranges of:

1.5 to 3.0 ng/ml inclusive and 7.5 to 9.0 ng/ml inclusive encompassing the ascertained AMH level for the subject that is under 36 years old, 2.5 to 4.0 ng/ml inclusive and 7.0 to 8.5 ng/ml inclusive encompassing the ascertained AMH level for the subject that is 36 to 38 years old inclusive, 2.0 to 4.5 ng/ml inclusive and 7.0 to 8.5 ng/ml inclusive encompassing the ascertained AMH level for the subject that is 39 to 40 years old inclusive, and 2.0 to 4.5 ng/ml inclusive and 7.0 to 8.5 ng/ml encompassing the ascertained AMH level for the subject that is 41 to 42 years old inclusive.

Further, the poor prognosis category pertains to both pregnancy probability and live birth probability and is in accord with AMH level ranges of:

0.0 to 1.0 ng/ml inclusive and 9.5 to 10.0 ng/ml inclusive encompassing the ascertained AMH level for the subject that is under 36 years old, 0.0 to 2.0 ng/ml inclusive and 9.0 to 10.0 ng/ml inclusive encompassing the ascertained AMH level for the subject that is 36 to 38 years old inclusive, 0.0 to 1.5 ng/ml inclusive and 9.0 to 10.0 ng/ml inclusive encompassing the ascertained AMH level for the subject that is 39 to 42 years old inclusive, and 0.0 to 10.0 ng/ml inclusive encompassing the ascertained AMH level for the subject that is over 42 years old.

In addition, the invention has applicability to the use of AMH antagonists having the opposite effects (i.e., AMH receptor blocking antibodies, AMH binding antibodies etc.). For example, using AMH antagonists for induction of ovulation in Polycystic Ovary (PCO) syndrome patients who have abnormally high serum AMH levels. Also, AMH may inhibit growth of some cancers including ovarian and prostate.

The present invention encompasses treatment of any species of subject, including, but not limited to humans and other primates, mammals including commercial relevant mammals such as cattle, pigs, horses, sheep, cats, dogs, rats, and mice. The treatment administers to a subject an effective amount of AMH protein to achieve and maintain an AMH level of between 3.5-8.5 ng/ml within the subject. The composition has a peptide that includes an amino acid sequent having at least a 95% identify to SEQ ID NO: 1. The sequence of AMH protein set forth in SEQ ID NO: 1 is found at the paragraph bridging pages 21-22 of provisional application Ser. No. 62/128,127 and copy thereof is supplied herein under the heading SEQUENCE LISTINGS and consist of the same material incorporated by reference in to the specification. The referent to 95% identity to SEQ ID NO: 1 is found at p. 32 of provisional Ser. No. 62/128,127 and is incorporated herein by reference.

It can be understood that FIGS. 3A and 3B in effect depict different types of analysis tools for ascertaining pregnancy percentage rates or pregnancy percentage probabilities with in vitro fertilization and that FIGS. 3C and 3D depict different types of analysis tools for ascertaining live birth percentage rates or live birth percentage probabilities.

The inventive method involves making a diagnosis with the analysis tool to provide a prognosis of a subject's probability of pregnancy success with in vitro fertilization or of success with live birth. The steps include ascertaining an anti-Müllerian hormone (AMH) level of the subject based upon results from an assay of a blood sample of the subject, accessing an analysis tool that identifies an applicable one of different prognosis categories that contains a corresponding success percentage for the ascertained AHM level of the subject based upon the age of the subject; and making a diagnosis from the accessed analysis tool as to a prognosis for success of either pregnancy with in vitro fertilization or live birth.

The analysis tool of FIGS. 3A, 3B, 3C and 3D sets forth success percentages that correlate with AMH levels based upon applicable age groups. The analysis tool assigns success percentages for either pregnancy rates (FIG. 3A) or pregnancy probabilities (FIG. 3B) or live birth rates (FIG. 3C) or live birth probabilities (FIG. 3D). The analysis tool categorizes the assigned success percentages into different groupings associated with different prognosis categories as per the different colored regions in FIGS. 3A and 3C.

For each of the different prognosis categories, the associated groupings of the success percentages each have a respective range of AMH levels for each age group. in FIGS. 3A and 3C.

While the foregoing description and drawings represent the preferred embodiments of the present invention, it will be understood that various changes and modifications may be made without departing from the scope of the present invention.

TABLE 1

Patient characteristics of patient Cohorts I, II and III

| | Cohort I | Cohort II | Cohort III |
|---|---|---|---|
| Cycles (n) | 1247 | 1514 | 632 |
| Embryos (n) | 4.9 ± 4.3 | 4.0 ± 3.4 | 4.1 ± 3.5 |
| Age (years) | 37.8 ± 6.7 | 39.5 ± 5.0 | 39.5 ± 4.9 |
| FSH (mIU/ml) | 17.3 ± 19.1 | 15.4 ± 14.8 | 15.8 ± 16.2 |
| AMH (ng/ml) | 1.1 ± 1.9 | 1.1 ± 1.9 | 1.1 ± 1.9 |
| Pregnancies (n) | 346 | 246 | 106 |
| (%) | 27.8 | 16.2 | 16.8 |
| Live births (n) | 264 | 178 | 73 |
| (%) | 21.2 | 11.8 | 11.6 |
| Miscarriages (n) | 82 | 68 | 33 |
| (%) | 23.7 | 27.6 | 31.1 |

TABLE 2

Cohorts I, II and III: Patient characteristics by age category

| Ages (years) | <36 | 36-38 | 39-40 | 41-42 | ≥43 |
|---|---|---|---|---|---|
| COHORT I | | | | | |
| Cycles (n) | 432 | 174 | 162 | 183 | 296 |
| Embryos (n) | 7.5 ± 5.1 | 3.7 ± 2.9 | 3.7 ± 2.9 | 3.3 ± 2.4 | 3.1 ± 2.2 |
| Pregnancies (n) | 203 | 49 | 40 | 32 | 22 |
| (%) | 47.0% | 28.2% | 24.7% | 17.5% | 7.4% |
| Live births (n) | 173 | 34 | 29 | 18 | 10 |
| (%) | 40.0% | 19.5% | 17.9% | 9.8% | 3.4% |
| Miscarriages (n) | 30 | 15 | 11 | 14 | 12 |
| (%) | 14.8% | 30.6% | 27.8% | 43.8% | 54.6% |
| COHORT II | | | | | |
| Cycles (n) | 303 | 234 | 239 | 259 | 479 |
| FSH (mIU/ml) | 11.8 ± 12.7 | 15.0 ± 14.1 | 15.5 ± 13.2 | 14.7 ± 14.2 | 18.0 ± 16.9 |
| Pregnancies (n) | 101 | 50 | 40 | 32 | 23 |
| (%) | 33.3% | 21.4% | 16.7% | 12.4% | 4.8% |

TABLE 2-continued

Cohorts I, II and III: Patient characteristics by age category

| Ages (years) | <36 | 36-38 | 39-40 | 41-42 | ≥43 |
| --- | --- | --- | --- | --- | --- |
| Live births (n) | 86 | 35 | 29 | 18 | 10 |
| (%) | 28.4% | 15.0% | 12.1% | 6.9% | 2.1% |
| Miscarriages (n) | 15 | 15 | 11 | 14 | 13 |
| (%) | 14.9% | 30.0% | 27.5% | 43.8% | 56.5% |
| COHORT III | | | | | |
| Cycles (n) | 127 | 87 | 103 | 109 | 206 |
| AMH (ng/ml) | 2.3 ± 3.3 | 1.1 ± 1.9 | 0.7 ± 1.0 | 0.6 ± 1.1 | 0.7 ± 0.7 |
| Pregnancies (n) | 45 | 16 | 16 | 14 | 15 |
| (%) | 35.4% | 18.4% | 15.5% | 12.8% | 7.3% |
| Live births (n) | 37 | 11 | 13 | 7 | 5 |
| (%) | 29.1% | 12.6% | 12.6% | 6.4% | 2.4% |
| Miscarriages (n) | 8 | 5 | 3 | 7 | 10 |
| (%) | 17.8% | 31.2% | 18.8% | 50.0% | 66.7% |

SEQUENCE LISTINGS (SEQ ID NO: 1)
1
MRDLPLTSLA LVLSALGALL GTEALRAEEP AVGTSGLIFR

EDLDWPPGSP QEPLCLVALG GDSNGSSSPL RVVGALSAYE

QAFLGAVQRA RWGPRDLATF GVCNTGDRQA ALPSLRRLGA

WLRDPGGQRL VVLHLEEVTW EPTPSLRFQE PPPGGAGPPE

LALLVLYPGP GPEVTVTRAG LPGAQSLCPS RDTRYLVLAV

DRPAGAWRGS GLALTLQPRG EDSRLSTARL QALLFGDDHR

CFTRMTPALL LLPRSEPAPL PAHGQLDTVP FPPPRPSAEL

EESPPSADPF LETLTRLVRA LRVPPARASA PRLALDPDAL

AGFPQGLVNL SDPAALERLL DGEEPLLLLL RPTAATTGDP

APLHDPTSAP WATALARRVA AELQAAAAEL RSLPGLPPAT

APLLARLLAL CPGGPGGLGD PLRALLLLKA LQGLRVEWRG

RDPRGPGRAQ RSAGATAADG PCALRELSVD LRAERSVLIP

ETYQANNCQG VCGWPQSDRN PRYGNHVVLL LKMQVRGAAL

ARPPCCVPTA YAGKLLISLS EERISAHHVP NMVATECGCR

What is claimed is:

1. A method of increasing a pregnancy rate in a subject, comprising:
   accessing an analysis tool that identifies an applicable one of different prognosis categories each containing a corresponding success percentage for an ascertained anti-Müllerian hormone (AMH) level of a subject based upon the age of the subject, wherein the analysis tool:
   sets forth a success percentage that is correlated with an AMH level based upon an applicable age group,
   assigns the success percentage as applicable to one of a live birth rate, a live birth probability, a pregnancy rate with in vitro fertilization and a pregnancy probability with in vitro fertilization, and
   categorizes the assigned success percentage into an associated grouping for an applicable one of different prognosis categories;
   making a diagnosis by retrieving the associated grouping from the accessed analysis tool so as to provide a prognosis for increasing the pregnancy rate in the subject;
   administering to the subject a composition having an effective amount of AMH protein to achieve and maintain the AMH level of between 3.5-8.5 ng/ml within the subject, wherein the effective amount of AMH in accord with the prognosis; and
   adjusting, over time, the effective amount of the AMH protein within the composition being administered accordingly to maintain the AMH level of between 3.5-8.5 ng/ml within the subject through testing of the AMH level of the subject over time
   wherein the composition comprises SEQ ID NO: 1.

2. The method of claim 1, wherein for each of the different prognosis categories, associating the associated grouping with a respective range of AMH levels in correspondence with an applicable one of the age groups.

3. The method of claim 1, further comprising:
   selecting the different prognosis categories from the group consisting of good, intermediate and poor prognosis categories; wherein the good prognosis category has a higher probability of pregnancy success with in vitro fertilization than that of the intermediate and poor prognosis categories, the poor prognosis category has a worse probability of pregnancy success with in vitro fertilization than that of the intermediate and good prognosis categories, and the intermediate prognosis category has a probability of pregnancy success with in vitro fertilization that is between that for the poor and good prognosis categories.

4. The method of claim 3, wherein the good prognosis category pertains to pregnancy probability and is in accord with AMH level ranges of: 3.5 to 8.5 ng/ml inclusive encompassing the ascertained AMH level for the subject that is under 36 years old, 4.5 to 7.5 ng/ml inclusive encompassing the ascertained AMH level for the subject that is 36 to 38 years old inclusive, 5.0 to 7.0 ng/ml inclusive encompassing the ascertained AMH level for the subject that is 39 to 42 years old inclusive, and 4.5 to 7.5 ng/ml inclusive encompassing the ascertained AMH level for the subject that is over 42 years old.

5. The method of claim 3, wherein the intermediate prognosis category pertains to pregnancy probability and is in accord with any of AMH level ranges of only: both a range of 1.0 to 3.0 ng/ml inclusive and a range of 9.0 to 10.0 ng/ml inclusive for encompassing the ascertained AMH level for the subject that is under 36 years old, both a range of 2.5 to 4.0 ng/ml inclusive and a range of 8.0 to 10.0 ng/ml inclusive for encompassing the ascertained AMH level for the subject that is 36 to 38 years old inclusive, both a range of 1.5 to 4.5 ng/ml inclusive and a range of 7.5 to 10.0 ng/ml inclusive for encompassing the ascertained AMH level for the subject that is 39 to 40 years old inclusive, both a range of 2.5 to 4.5 ng/ml inclusive and a range of 7.5 to 10.0 ng/ml for encompassing the ascertained AMH level for the subject that is 41 to 42 years old inclusive, and both a range of 3.0 to 4.0 ng/ml inclusive and a range of 8.0 to 10.0 ng/ml inclusive for encompassing the ascertained AMH level for the subject that is over 42 years old.

6. The method of claim 3, wherein the poor prognosis category pertains to pregnancy probability and is in accord with AMH level ranges of: a range of 0.0 to 0.5 ng/ml inclusive for encompassing the ascertained AMH level for the subject that is under 36 years old, a range of 0.0 to 2.0 ng/ml inclusive for encompassing the ascertained AMH level for the subject that is 36 to 38 years old inclusive, a range of 0.0 to 1.0 ng/ml inclusive for encompassing the ascertained AMH level for the subject that is 39 to 40 years old inclusive, a range of 0.0 to 2.0 ng/ml inclusive for encompassing the ascertained AMH level for the subject that is 41 to 42 years old inclusive, and a range of 0.0 to 2.5 ng/ml inclusive for encompassing the ascertained AMH level for the subject that is over 42 years old.

7. The method of claim 1, wherein the administering occurs for a period of time and with dosages, the period of time being selected from the category consisting of about 1 day to about 180 days, 10 days to about 120 days and 30 days to about 90 days, and the dosages being within a range selected from the category consisting of about 100 ng per day to about 44,000 ng per day, and about 22,000 ng per day to about 44,000 ng per day.

8. The method of claim 1, further comprising:
ceasing the administering after a period of time; inducing superovulation in the subject after the period of time ends; and
resuming the administrating administering as warranted to maintain the AMH level after a further period of time elapses subsequent to commencement of inducing superovulation.

9. The method of claim 8, wherein the inducing superovulation in the subject is carried out by administering to the subject at least one agent selected from the category consisting of follicle stimulating hormone (FSH), luteinizing hormone (LH), clomiphene, a selective estrogen-receptor modulator (SERM) and an aromatase inhibitor.

10. The method of claim 1, wherein the administering to the subject of the effective amount of AMH to achieve and maintain the AMH level is within a range of: 3.5-8.5 ng/ml for the subject being under 36 years old; 4.5-7.5 ng/ml for the subject being 36-38 years old inclusive; 5.0-7.0 ng/ml for the subject being 39-42 years old inclusive; and 4.5-7.5 ng/ml for the subject being over 42 years old.

11. A method of increasing a live birth rate in a subject, comprising:
accessing an analysis tool that identifies an applicable one of different prognosis categories each containing a corresponding success percentage for an ascertained anti-Mü llerian hormone (AMH) level of a subject based upon the age of the subject, wherein the analysis tool:
sets forth a success percentage that is correlated with an AMH level based upon an applicable age group,
assigns the success percentage as applicable to a live birth rate, a live birth probability, a pregnancy rate with in vitro fertilization and a pregnancy probability with in vitro fertilization, and
categorizes the assigned success percentage into an associated grouping for an applicable one of different prognosis categories;
making a diagnosis by retrieving the associated grouping from the accessed analysis tool so as to provide a prognosis for increasing the live birth rate in the subject; and
administering to the subject a composition having an effective amount of AMH protein in accord with the prognosis to achieve and maintain the AMH level over time of between: 5.0-6.5 ng/ml inclusive for the subject who is between 39-42 years old, 4.5-6.5 ng/ml inclusive for the subject who is between 36-38 years old, and 3.5-7.0 ng/ml for the subject who is under 36 years old, wherein the composition comprises SEQ ID NO: 1.

12. The method of claim 11, further comprising:
selecting the different prognosis categories from the group consisting of good, intermediate and poor prognosis categories, wherein the good prognosis category has a higher probability of live birth success than that of the intermediate and poor prognosis categories, the poor prognosis category has a worse probability of live birth success than that of the intermediate and good prognosis categories, and the intermediate prognosis category has a probability of live birth success that is between that for the poor and good prognosis categories.

13. The method of claim 12, wherein the good prognosis category pertains to live birth probability and is in accord with AMH level ranges of: a range of 3.5 to 7.0 ng/ml inclusive for encompassing the ascertained AMH level for the subject that is under 36 years old, a range of 4.5 to 6.5 ng/ml inclusive for encompassing the ascertained AMH level for the subject that is 36 to 38 years old inclusive, and a range of 5.0 to 6.5 ng/ml inclusive for encompassing the ascertained AMH level for the subject that is 39 to 42 years old inclusive.

14. The method of claim 12, wherein the intermediate prognosis category pertains to live birth probability and is in accord with AMH level ranges of: both a range of 1.5 to 3.0 ng/ml inclusive and a range of 7.5 to 9.0 ng/ml inclusive for encompassing the ascertained AMH level for the subject that is under 36 years old, both a range of 2.5 to 4.0 ng/ml inclusive and a range of 7.0 to 8.5 ng/ml inclusive for encompassing the ascertained AMH level for the subject that is 36 to 38 years old inclusive, both a range of 2.0 to 4.5 ng/ml inclusive and a range of 7.0 to 8.5 ng/ml inclusive for encompassing the ascertained AMH level for the subject that is 39 to 40 years old inclusive, and both a range of 2.0 to 4.5 ng/ml inclusive and a range of 7.0 to 8.5 ng/ml for encompassing the ascertained AMH level for the subject that is 41 to 42 years old inclusive.

15. The method of claim 12, wherein the poor prognosis category pertains to live birth probability and is in accord with AMH level ranges of: both a range of 0.0 to 1.0 ng/ml inclusive and a range of 9.5 to 10.0 ng/ml inclusive for encompassing the ascertained AMH level for the subject that is under 36 years old, both a range of 0.0 to 2.0 ng/ml inclusive and a range of 9.0 to 10.0 ng/ml inclusive for encompassing the ascertained AMH level for the subject that is 36 to 38 years old inclusive, both a range of 0.0 to 1.5 ng/ml inclusive and a range of 9.0 to 10.0 ng/ml inclusive for encompassing the ascertained AMH level for the subject that is 39 to 42 years old inclusive, and a range of 0.0 to 10.0 ng/ml inclusive for encompassing the ascertained AMH level for the subject that is over 42 years old.

16. A method of terminating pregnancy or increasing miscarriage rate in a subject, comprising:
   accessing an analysis tool that identifies an applicable one of different prognosis categories each containing a corresponding success percentage for an ascertained anti-Müllerian hormone (AMH) level of a subject based upon the age of the subject, wherein the analysis tool:
      sets forth a success percentage that is correlated with an AMH level based upon an applicable age group,
      assigns the success percentage as applicable to a live birth rate, a live birth probability, a pregnancy rate with in vitro fertilization and a pregnancy probability with in vitro fertilization, and
      categorizes the assigned success percentage into an associated grouping of the assigned success percentage for an applicable one of different prognosis categories;
   making a diagnosis by retrieving the associated grouping from the accessed analysis tool so as to provide a prognosis for terminating pregnancy or increasing miscarriage rate in the subject; and
   administering to the subject a composition having an effective amount of AMH protein in accord with the prognosis to achieve and maintain an AMH level that is higher than that of: 7.0 ng/ml for the subject being under 36 years old; and 6.5 ng/ml for the subject being 36-42 years old inclusive,
   wherein the composition comprises SEQ ID NO: 1.

17. A method of decreasing a pregnancy rate in a subject, comprising:
   accessing an analysis tool that identifies an applicable one of different prognosis categories each containing a corresponding success percentage for an ascertained anti-Müllerian hormone (AMH) level of a subject based upon the age of the subject, wherein the analysis tool:
      sets forth a success percentage that is correlated with an AMH level based upon an applicable age group,
      assigns the success percentage as applicable to a live birth rate, a live birth probability, a pregnancy rate with in vitro fertilization and a pregnancy probability with in vitro fertilization, and
      categorizes the assigned success percentage into an associated grouping for an applicable one of different prognosis categories;
   making a diagnosis by retrieving the associated grouping from the accessed analysis tool so as to provide a prognosis for decreasing the pregnancy rate in the subject; and
   administering to the subject a composition having an effective amount of AMH protein in accord with the prognosis to achieve and maintain an AMH level that is higher than that of: 8.5 ng/ml for the subject being under 36 years old; 7.5 ng/ml for the subject being 36-38 years old inclusive; 7.0 ng/ml for the subject being 39-42 years old inclusive; and 7.5 ng/ml for the subject being over 42 years old,
   wherein the composition comprises SEQ ID NO: 1.

* * * * *